United States Patent [19]
Durmowicz et al.

[11] Patent Number: 5,962,273
[45] Date of Patent: Oct. 5, 1999

[54] DETECTION OF NEISSERIA GONORRHOEAE BY AMPLIFICATION AND DETECTION OF ITS NUCLEIC ACID

[75] Inventors: Gerard P. Durmowicz, Cockeysville; James M. Harris, Columbia; Karen Dilly Yanson, Towson, all of Md.

[73] Assignee: Becton Dickinson and Company, Franklin Lakes, N.J.

[21] Appl. No.: 08/963,946

[22] Filed: Nov. 4, 1997

[51] Int. Cl.[6] .............................. C12Q 1/68; C12P 19/34; C07H 21/04; C07H 21/00

[52] U.S. Cl. ........................... 435/91.1; 435/6; 435/91.2; 536/22.1; 536/24.3; 536/25.3; 536/25.32

[58] Field of Search ................................. 536/22.1, 24.3, 536/25.3, 25.32, 91.1; 435/91.2, 6

[56] References Cited

U.S. PATENT DOCUMENTS

| | | | |
|---|---|---|---|
| 4,755,458 | 7/1988 | Rabbani et al. | 435/5 |
| 5,108,895 | 4/1992 | Woods et al. | 435/6 |
| 5,453,355 | 9/1995 | Birkenmeyer et al. | 435/6 |

FOREIGN PATENT DOCUMENTS

| | | |
|---|---|---|
| 0 353 985 A2 | 7/1990 | European Pat. Off. . |
| 0 317 077 B1 | 1/1996 | European Pat. Off. . |

OTHER PUBLICATIONS

Donegan, James J., Isolation of a species–specific DNA probe for Neisseria gonorrhoeae using a novel technique particularly suitable for use with closely related species displaying high levels of DNA homology; *Moll. Cell. Prob.*, 3, pp. 13–26 (1989).

Walker, G.T. et al., Isothermal in vitro amplification of DNA by a restriction enzyme/DNA polymerase system; *PNAS*, 89, pp. 392–396 (1992).

Walker, G.T. et al., Strand displacement amplification—an isothermal, in vitro DNA amplification technique, *Nucl. Acids Res.*, 20, pp. 1691–1696 (1992).

Database search report, Accesion No. U65994, 1996.

*Primary Examiner*—Kenneth R. Horlick
*Assistant Examiner*—Joyce Tung
*Attorney, Agent, or Firm*—David W. Highet, Esq.

[57] ABSTRACT

Methods for detecting the presence of *Neisseria gonorrhoeae* are described. These methods are based upon amplifying a portion of the *Neisseria gonorrhoeae* genome and detecting the presence of the amplified nucleic acid. Various sets of primers and detectors are disclosed. The disclosed primers and detectors can be used in Strand Displacement Amplification assays, thermal Strand Displacement Amplification Assays, and homogeneous, fluorescent real time thermal Strand Displacement Amplification assays to specifically detect the presence of *Neisseria gonorrhoeae* even in the presence of contaminating microorganisms and in the presence of human DNA.

58 Claims, 3 Drawing Sheets

Alignment of GCIR5 Primers and Detectors:

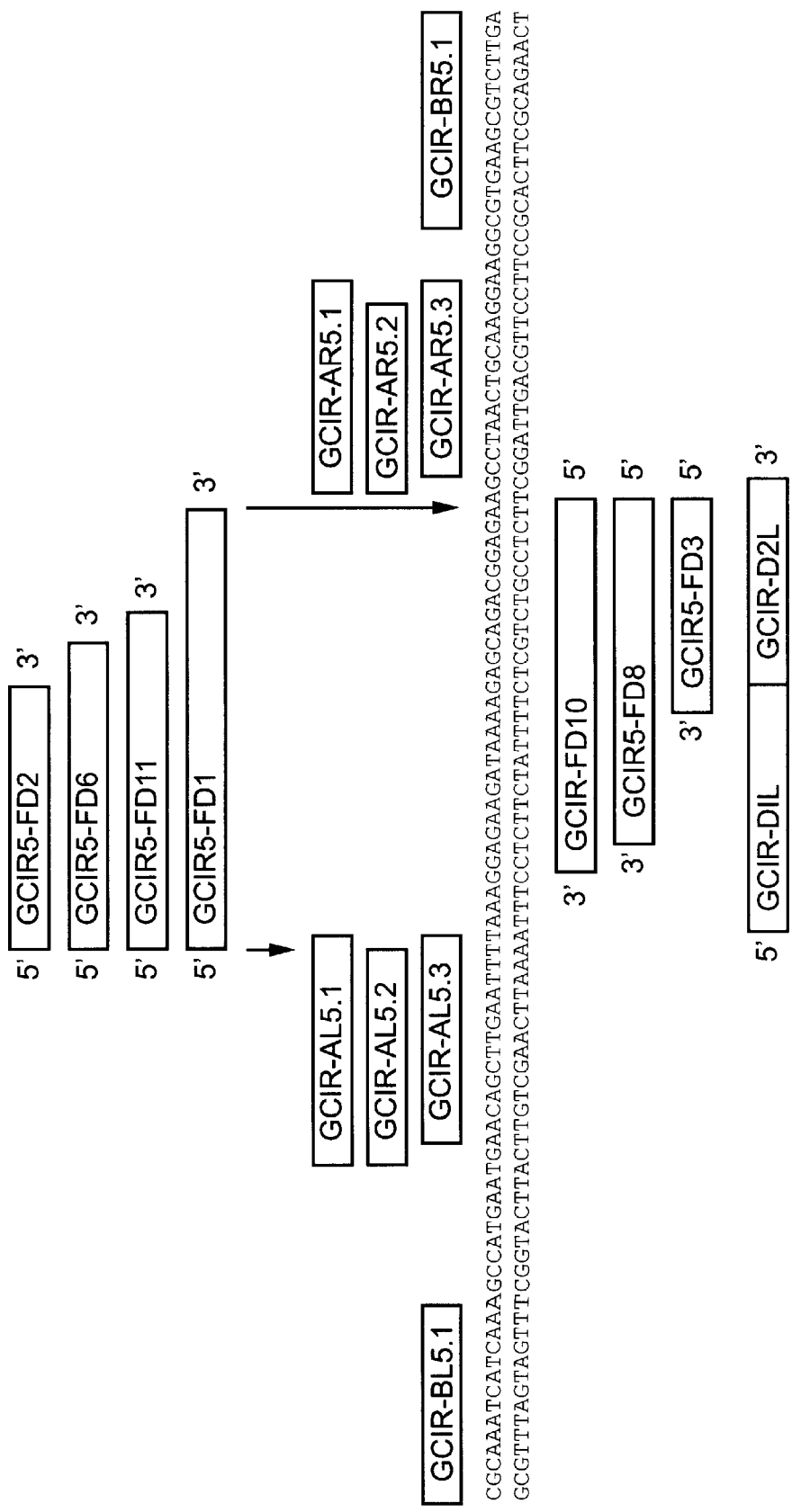
FIG-1 Alignment of GCIR5 Primers and Detectors:

FIG-2 Alignment of GCIR5 Primers and Detectors:

GAGAAGATAAAAGAGACGAGAAGCCTAACTGCAAGGAAGGCGTGAAGCGTCTTGAAACCATACCGGCAATAGGCAGAATGACCGCAGCCGTATTGT
CTCTTCTATTTTCTCGTCTTCGGATTGACGTTCCTTCCGCTCTTCGCAGAACTTTGGTATGGCCGTTATCCGTCTTACTGGCGTCGGGCATAACA

FIG-3  Alignment of GCO2 Bumpers, Primers, and Detectors

TTTCCCGACTTCATCCAAAAGGCTGAAGAAAAGAAGAAGCCTAAAAAAGTCATCATCGCAGCATTGATGCGTAAACTCGCCGTTATTGCGTATCAC

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:1:

CTGATATCTG CATGGAGGCA A                                                  21

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:2:

GATCGTAATC TCCGCCTTTC TT                                                 22

(2) INFORMATION FOR SEQ ID NO:3:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:3:

CCGCAGCATA CGCGCAAATC AA                                                 22

(2) INFORMATION FOR SEQ ID NO:4:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:4:

GGTATGGTTT CAAGACGCTT CA                                                 22

(2) INFORMATION FOR SEQ ID NO:5:

(i) SEQUENCE CHARACTERISTICS:
       (A) LENGTH: 41 base pairs
       (B) TYPE: nucleic acid
       (C) STRANDEDNESS: single
       (D) TOPOLOGY: linear (xi) SEQUENCE DESCRIPTION: SEQ ID NO:5:

CGATTCCGCT CCAGACTTCT CGGGGAACAG CTTGAAGTTT T                            41

(2) INFORMATION FOR SEQ ID NO:6:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (xi) SEQUENCE DESCRIPTION: SEQ ID NO:6:

CGATTCCGCT CCAGACTTCT CGGGGAACAG CTTGAAGTTT                          40

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:7:

CGATTCCGCT CCAGACTTCT CGGGAACAGC TTGAAGTTTT                          40

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:8:

ACCGCATCGA ATGCATGTCT CGGGTCCTTG CAGTTAGGC                           39

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:9:

ACCGCATCGA ATGCATGTCT CGGGCCTTGC AGTTAGGC                            38

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:10:

ACCGCATCGA ATGCATGTCT CGGGTCCTTG CAGTTAGG                            38

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:11:

CGCAAATCAT CAAAG                                                     15

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

TCAAGACGCT TCACG                                                        15

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:13:

AAAGGAGAAG ATAAAAG                                                      17

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:14:

AGCAGACGGA GAAG                                                         14

(2) INFORMATION FOR SEQ ID NO:15:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:15:

TAGCACCCGA GTGCTTTCTC CGTCTGCTCT TTTATCTTCT C                            41

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:16:

TAGCACCCGA GTGCTTTCTC CGTCTGCTCT TTTATCTTC                               39

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

TAGCACCCGA GTGCTTTCTC CGTCTGCTCT                                         30

(2) INFORMATION FOR SEQ ID NO:18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:18:

TAGCACCCGA GTGCTTAAAG GAGAAGATAA AAGAGCAG                                38

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:19:

TAGACCCGAG TGCTTAAAGG AGAAGATAAA AGAGC                            35

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

TAGCACCCGA GTGCTTAAAG GAGAAGATAA AAG                              33

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:21:

TAGCACCCGA GTGCTTAAAG GAGAAGATAA AAGAGCAGAC GGAGA                45

(2) INFORMATION FOR SEQ ID NO:22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:22:

CGATTCCGCT CCAGACTTCT CGGGGAGAAG CCTAACTG                         38

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:23:

CGATTCCGCT CCAGACTTCT CGGGAGAAGC CTAACTGCA                        39

(2) INFORMATION FOR SEQ ID NO:24:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:24:

ACCGCATCGA ATGCATGTCT CGGGCTGCCT ATTGCCGGT                        39

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:25:

ACCGCATCGA ATGCATGTCT CGGGTGCCTA TTGCCGGTA                              39

(2) INFORMATION FOR SEQ ID NO:26:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:26:

ACCGCATCGA ATGCATGTCT CGGGTGCCTA TTGCCGGT                               38

(2) INFORMATION FOR SEQ ID NO:27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:27:

GAGAAGATAA AAGAG                                                        15

(2) INFORMATION FOR SEQ ID NO:28:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:28:

ACAATACGGC TGCG                                                         14

(2) INFORMATION FOR SEQ ID NO:29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:29:

CAAGGAAGGC GTGAA                                                        15

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:30:

GCGTCTTGAA ACCAT                                                        15

(2) INFORMATION FOR SEQ ID NO:31:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (xi) SEQUENCE DESCRIPTION: SEQ ID NO:31:

TAGCACCCGA GTGCTGGAAG GCGTGAAGCG TCTTGAAACC AT                               42

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:32:

CGATTCCGCT CCAGACTTCT CGGGAGGCTG GAAGAAAAG                                  39

(2) INFORMATION FOR SEQ ID NO:33:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:33:

CGATTCCGCT CCAGACTTCT CGGGGGCTGG AAGAAAAG                                   38

(2) INFORMATION FOR SEQ ID NO:34:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:34:

ACCGCATCGA ATGCATGTCT CGGGCGAGTT TACGCATCAA                                 40

(2) INFORMATION FOR SEQ ID NO:35:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:35:

ACCGCATCGA ATGCATGTCT CGGGGAGTTT ACGCATCAA                                  39

(2) INFORMATION FOR SEQ ID NO:36:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:36:

TTTCCCCGAC TTCA                                                             14

(2) INFORMATION FOR SEQ ID NO:37:

(i) SEQUENCE CHARACTERISTICS:
        (A) LENGTH: 15 base pairs

```
            (B) TYPE: nucleic acid
            (C) STRANDEDNESS: single
            (D) TOPOLOGY: linear (xi) SEQUENCE DESCRIPTION: SEQ ID NO:37:

GTGATACGCA ATAAC                                                          15

(2) INFORMATION FOR SEQ ID NO:38:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:38:

AAGAAGCCTA AAAAAG                                                         16

(2) INFORMATION FOR SEQ ID NO:39:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:39:

TCATCATCGC AGCA                                                           14
```

DETECTION OF NEISSERIA GONORRHOEAE BY AMPLIFICATION AND DETECTION OF ITS NUCLEIC ACID

FIELD OF THE INVENTION

The present invention relates to methods for determining the presence or absence of *Neisseria gonorrhoeae* in patients. The method involves using nucleic acid primers to amplify specifically DNA of *Neisseria gonorrhoeae*, preferably using the technique of Strand Displacement Amplification (SDA), thermophilic Strand Displacement Amplification (tSDA) or fluorescent real time tSDA.

BACKGROUND OF THE INVENTION

*Neisseria gonorrhoeae* is the causative agent of the sexually transmitted disease gonorrhea. It is one of the most prevalent sexually transmitted diseases reported in humans despite antibiotic treatment. Diagnosis and detection of this organism is still dependent on overnight culture of clinical swabs followed by biochemical and/or microscopic identification. *N. gonorrhoeae* shares an extremely high degree of homology with other closely related Neisseria species. This poses a difficult problem when trying to design primers that are specific for *N. gonorrhoeae*. This invention describes the development of *N. gonorrhoeae* specific primers used in thermophilic Strand Displacement Amplification (tSDA).

Several *N. gonorrhoeae* specific DNA fragments were identified by Donegan et al. via a "sandwich hybridization" screen of an M13 library derived from *N. gonorrhoeae* genomic DNA (Donegan et al., *Mol. Cell. Prob.* 3:13–26 (1989); U.S. Pat. No. 4,755,458). One of these fragments was further mapped and characterized in U.S. Pat. No. 5,108,895.

Oligonucleotide probe based assays such as Southern hybridizations or dot blots are capable of returning a rapid result (i.e., in one day or less) for diagnosis of bacterial infections. Assays based on amplification of nucleic acids are usually more sensitive and may provide even more rapid results, often within hours. For diagnosis of *N. gonorrhoeae* infections such methods require development of oligonucleotide probes or primers which are specific for this species.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 5' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *PNAS* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. As the target binding sequence is the portion of a primer which determines its target-specificity, for amplification methods which do not require specialized sequences at the ends of the target the amplification primer generally consists essentially of only the target binding sequence. For amplification methods which require specialized sequences appended to the target other than the nickable restriction endonuclease recognition site and the tail of SDA (e.g., an RNA polymerase promoter for 3SR, NASBA or transcription based amplification), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization in a species of organism or a group of related species without substantial detection, amplification or oligonucleotide hybridization in other species of the same genus or species of a different genus.

The term assay probe refers to any oligonucleotide used to facilitate detection or identification of a nucleic acid. For example, in the present invention, assay probes are used for detection or identification of *Neisseria gonorrhoeae* nucleic acids. Detector probes, detector primers, capture probes and primers as described below are examples of assay probes.

SUMMARY OF THE INVENTION

The present invention provides oligonucleotides useful as amplification primers and assay probes for species-specific detection and identification of *Neisseria gonorrhoeae*. Species-specificity means that the inventive primers amplify a target sequence in *Neisseria gonorrhoeae* nucleic acids with little or no detectable amplification of target sequences of other species of closely related microorganisms. The primers of the invention uniquely amplify the target sequence in *Neisseria gonorrhoeae* but not in other bacteria thereby allowing sensitive detection and identification of *Neisseria gonorrhoeae*. Optimization of the primers for use in tSDA permits increased amplification efficiency in shorter reaction times.

The oligonucleotides of the invention may be used after culture as a means for confirming the identity of the cultured organism. Alternatively, they may be used prior to culture or in place of culture for detection and identification of *Neis-* seria gonorrhoeae nucleic acids using known amplification methods. In either case, the inventive oligonucleotides and assay methods provide a means for rapidly discriminating between the nucleic acids of Neisseria gonorrhoeae and other species of bacteria, allowing the practitioner to identify rapidly this microorganism without resorting to the time-consuming phenotypic and biochemical procedures customarily relied upon. Such rapid identification of the specific etiological agent involved in a bacterial infection provides information which can be used to determine appropriate therapy within a short period of time.

BRIEF DESCRIPTION OF THE DRAWINGS

The various objects, advantages and novel features of the present invention will be readily understood from the following detailed description when read in conjunction with the appended drawings in which:

FIG. 1 illustrates the relative locations of the system GCIR5 primers, bumpers and detectors across a 103 base pair region.

FIG. 2 illustrates the relative locations of the system GCIRSL primers, bumpers and detectors across a 100 base pair region.

FIG. 3 illustrates the relative locations of the GC O2 primers, bumpers and detectors across a 98 base pair region.

DETAILED DESCRIPTION OF THE INVENTION

The present invention provides oligonucleotides, amplification primers and assay probes which exhibit Neisseria gonorrhoeae specificity in nucleic acid amplification reactions. Also provided are methods for detecting and identifying Neisseria gonorrhoeae nucleic acids using the oligonucleotides of the invention. Preferred methods are to use the oligonucleotides in tSDA and homogeneous real time fluorescent tSDA reactions. These methods are taught in U.S. Pat. No. 5,547,861, U.S. Pat. No. 5,648,211, U.S. patent application Ser. No. 08/865,675, filed May 30, 1997 and U.S. patent application Ser. No. 08/855,085, filed May 13, 1997 the disclosures of which are specifically incorporated herein by reference.

The present invention provides three tSDA systems (GCIR5, GCIRSL and GC O2) that specifically amplify and detect N. gonorrhoeae genomic DNA. Several primer combinations were designed for each system and tested in statistically designed experiments. Specificity, sensitivity and crossreactivity experiments were performed with the best primer combination for each system.

Sequence analysis was conducted on a 800 bp region of N. gonorrhoeae genomic DNA.

The 800 bp region was generated using primers GC 1.3 5'-CTGATATCTGCATGGAGGCAA-3' (SEQ ID NO: 1) and GC 2.3 5'-GATCGTAATCTCCGCCTTTCTT-3' (SEQ ID NO: 2), and a 200 bp region internal thereto was generated using primers IR.R.2 5'-CCGCAGCATACGCGCAAATCAA-3' (SEQ ID NO: 3) and IRLI 5'- GGTATGGTTTCAAGACGCTTCA-3' (SEQ ID NO: 4). Mapping of the 800 bp fragment revealed several regions of complete specificity when tested with several N. gonorrhoeae strains as well as other related Neisseria species. However, several regions of crossreactivity with Neisseria species were identified within this fragment. Based on this information, the 3 tSDA systems were designed.

Primers were designed based on the 800 bp fragment of Neisseria gonorrhoeae nucleic acid. Primer combinations were screened for optimal conditions. Various detector probes were tested for specificity and sensitivity in tSDA reactions and in fluorescent real time tSDA reactions.

As nucleic acids do not require complete complementarity in order to hybridize, it is to be understood that the probe and primer sequences herein disclosed may be modified to some extent without loss of utility as Neisseria gonorrhoeae-specific probes and primers. As is known in the art, hybridization of complementary and partially complementary nucleic acid sequences may be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain Neisseria gonorrhoeae specificity require only routine experimentation and are within the ordinary skill in the art.

The amplification products generated using the inventive primers may be detected by a characteristic size, for example on polyacrylamide or agarose gels stained with ethidium bromide. Alternatively, amplified N. gonorrhoeae target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al., Nucl. Acids Res., supra (a detector primer) or by hybridization, extension and conversion to double stranded form as described in EP 0 678 582 (a signal primer). Preferably, the assay probe is selected to hybridize to a sequence in the target which is between the amplification primers, i.e., it should be an internal assay probe. Alternatively, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Ligands are also useful immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

For commercial convenience, amplification primers for specific detection and identification of N. gonorrhoeae nucleic acids may be packaged in the form of a kit. Typically, such a kit contains at least one pair of amplification primers according to the present invention. Reagents for performing a nucleic acid amplification reaction may also be included with the N. gonorrhoeae-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

The target binding sequences of the amplification primers in conjunction with detector probes can confer species hybridization specificity on the oligonucleotides and therefore provide species-specificity to an amplification based assay. Other sequences, as required for performance of a selected amplification reaction, may optionally be added to the target binding sequences disclosed herein without altering the species-specificity of the oligonucleotide. By way of example, the N. gonorrhoeae-specific amplification primers of the invention may contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 315. Preferably, the recognition site is for a thermophilic restriction endonuclease so that the amplification reaction may be performed under the conditions of thermophilic SDA (tSDA). Similarly, the tail sequence of the amplification primer (5' to the restriction endonuclease recognition site) is generally not critical, although the restriction site used for SDA and sequences which will hybridize either to their own target binding sequence or to the other primers should be avoided. Amplification primers for SDA according to the invention therefore consist of the 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions, the amplification primers according to the invention may consist of the disclosed target binding sequences only (e.g., for PCR) or the target binding sequence and additional sequences required for the selected amplification reaction (e.g., sequences required for SDA as described above or a promoter recognized by RNA polymerase for 3SR).

In SDA, the bumper primers are not essential for species-specificity, as they function to displace the downstream, species-specific amplification primers. It is only required that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence. However, the bumper primers described herein are species-specific for N. gonorrhoeae and may therefore also be used as target binding sequences in amplification primers, if desired.

Amplification reactions employing the primers of the invention may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (Ugi) prior to performing the subsequent amplification to prevent excision of dU in newly-formed amplification products.

Other systems were developed for performing tSDA using different combinations of primers, bumpers and detectors. However, these other systems were not preferred for various reasons such as lack of adequate specificity, narrow range of optimal conditions and lack of robustness.

The systems which were found to be useful for performing homogeneous nucleic acid amplification and real time detection of N. gonorrhoeae nucleic acid sequences were developed from the following primers and detectors.

GCIR5 Primers and Detectors

| Primers | Sequence |
| --- | --- |
| Amp. Upstream | |
| GCIR-AL5.1 | 5'CGATTCCGCTCCAGACTTCTCGGGGAACAGCTTGAAGTTTT3' (SEQ ID NO: 5) |
| GCIR-AL5.2 | 5'CGATTCCGCTCCAGACTTCTCGGGGAACAGCTTGAAGTTT3' (SEQ ID NO: 6) |
| GCIR-AL5.3 | 5'CGATTCCGCTCCAGACTTCTCGGGAACAGCTTGAAGTTTT3' (SEQ ID NO: 7) |
| Amp. Downstream: | |
| GCIR-AR5.1 | 5'ACCGCATCGAATGCATGTCTCGGGTCCTTGCAGTTAGGC3' (SEQ ID NO: 8) |

-continued

| Primers | Sequence |
|---|---|
| GCIR-AR5.2 | 5'ACCGCATCGAATGCATGTCTCGGGCCTTGCAGTTAGGC3' (SEQ ID NO: 9) |
| GCIR-AR5.3 | 5'ACCGCATCGAATGCATGTCTCGGGTCCTTGCAGTTAGG3' (SEQ ID NO: 10) |
| Bumpers: | |
| GCIR-BL5.1 | 5'CGCAAATCATCAAAG3' (SEQ ID NO: 11) |
| GCIR-BR5.1 | 5'TCAAGACGCTTCACG3' (SEQ ID NO: 12) |
| Detectors: | |
| GCIR-D1L | 5'AAAGGAGAAGATAAAAG3' (SEQ ID NO: 13) |
| GCIR-D2L | 5'AGCAGACGGAGAAG3' (SEQ ID NO: 14) |
| Fluorescent Detectors: | |
| Downstream | |
| GCIR5-FD10 | 5'TAGCACCCGAGTGCTTTCTCCGTCTGCTCTTTTATCTTCTC3' (SEQ ID NO: 15) |
| GCIR5-FD8 | 5' TAGCACCCGAGTGCTTTCTCCGTCTGCTCTTTTATCTTC3' (SEQ ID NO: 16) |
| GCIR5-FD3 | 5' TAGCACCCGAGTGCTTTCTCCGTCTGCTCT3' (SEQ ID NO: 17) |
| Upstream | |
| GCIR5-FD11 | 5'TAGCACCCGAGTGCTTAAAGGAGAAGATAAAAGAGCAG3' (SEQ ID NO: 18) |
| GCIR5-FD6 | 5'TAGCACCCGAGTGCTTAAAGGAGAAGATAAAAGAGC3' (SEQ ID NO: 19) |
| GCIR5-FD2 | 5'TAGCACCCGAGTGCTTAAAGGAGAAGATAAAAG3' (SEQ ID NO: 20) |
| GCIR5-FD1 | 5'TAGCACCCGAGTGCTTAAAGGAGAAGATAAAAGAGCAGACGGAGA3' (SEQ ID NO: 21) |

GCIRSL Primers and Detectors

| Primers | Sequence |
|---|---|
| Amp. Upstream | |
| GCIRSL.APL1 | 5'-CGATTCCGCTCCAGACTTCTCGGGGAGAAGCCTAACTG-3' (SEQ ID NO: 22) |
| GCIRSL.APL2 | 5'-CGATTCCGCTCCAGACTTCTCGGGAGAAGCCTAACTGCA-3' (SEQ ID NO: 23) |
| Amp Downstream | |
| GCIRSL.APR1 | 5'-ACCGCATCGAATGCATGTCTCGGGCTGCCTATTGCCGGT-3' (SEQ ID NO: 24) |
| GCIRSL.APR2 | 5'-ACCGCATCGAATGCATGTCTCGGGTGCCTATTGCCGGTA-3' (SEQ ID NO: 25) |
| GCIRSL.APR3 | 5'-ACCGCATCGAATGCATGTCTCGGGTGCCTATTGCCGGT-3' (SEQ ID NO: 26) |
| Bumpers | |
| GCIRSL.BL | 5'-GAGAAGATAAAAGAG-3' (SEQ ID NO: 27) |
| GCIRSL.BR | 5'-ACAATACGGCTGCG-3' (SEQ ID NO: 28) |
| Detectors | |
| GCIRSL.DL1 | 5'-CAAGGAAGGCGTGAA-3' (SEQ ID NO: 29) |
| GCIRSL.DL2 | 5'-GCGTCTTGAAACCAT-3' (SEQ ID NO: 30) |
| Fluorescent Detector | |
| GCIRSL.FD1 | 5'-TAGCACCCGAGTGCTGGAAGGCGTGAAGCGTCTTGAAACCAT-3' (SEQ ID NO: 31) |

GC O2 Primers and Detectors

| Primers | Sequence |
|---|---|
| Amp. Upstream | |
| O2AL44.1 | 5'-CGATTCCGCTCCAGACTTCTCGGGAGGCTGGAAGAAAAG-3' (SEQ ID NO: 32) |

-continued

| Primers | Sequence |
|---|---|
| 02AL42.1 | 5'-CGATTCCGCTCCAGACTTCTCGGGGGCTGGAAGAAAAG-3' (SEQ ID NO: 33) |
| Amp Downstream | |
| 02AR46.1 | 5'-ACCGCATCGAATGCATGTCTCGGGCGAGTTTACGCATCAA-3' (SEQ ID NO: 34) |
| 02AR42.1 | 5'-ACCGCATCGAATGCATGTCTCGGGGAGTTTACGCATCAA-3' (SEQ ID NO: 35) |
| Bumpers | |
| 02BL42.1 | 5'-TTT CCC CGA CTT CA-3' (SEQ ID NO: 36) |
| 02BR42.1 | 5'-GTG ATA CGC AAT AAC-3' (SEQ ID NO: 37) |
| Detectors | |
| 02DL42.1 | 5'-AAG AAG CCT AAA AAA G-3' (SEQ ID NO: 38) |
| 02DR42.1 | 5'-TCA TCA TCG CAG CA-3' (SEQ ID NO: 39) |

Assays for *Neisseria gonorrhoea* were performed using the technique of fluorescent real time tSDA. The primers, bumpers, and detectors designed for GCIR5 and GCIRSL are shown in FIG. 1 and FIG. 2, respectively. The annealing regions for the amplification primers and fluorescent detectors are represented by the rectangles above or below the DNA sequence. The conditions for fluorescent GCIR5 and GCIRSL tSDA were continually modified to achieve optimal sensitivity. Set forth below is one such set of optimal conditions for GCIR5 and one such set of optimal conditions for GCIRSL.

GCIR5:
7% glycerol
8% DMSO
45 mM potassium phosphate
(0.1 mM) dATP, (0.1 mM) dGTP, (0.25 mM) dUTP, (0.7 mM) alpha-thio dCTP
5 mM Magnesium acetate
100 ug/ml BSA
1.82% Trehalose
360 uM DTT
2400 ng human DNA
320 units BsoBI restriction endonuclease
20 units Bst polymerase
1 Unit Uracil-N-glycosylase
5 Units Uracil-N-glycosylase inhibitor
200 nM detector (FD10) (SEQ ID NO: 15)
500 nM amplification primers (GCIR-AL5.3 (SEQ ID NO: 7) and GCIR-AR5.1 (SEQ ID NO: 8))
50 nM bumpers (GCIR-BL5.1 (SEQ ID NO: 11) and GCIR-BR5.1 (SEQ ID NO: 12))
100 ul reaction volume
Decontamination performed for 20 minutes at 45° C.
Amplification performed for 60 minutes at 52° C.

GCIRSL:
7% Glycerol
5% DMSO
25 mM potassium phosphate
(0.2 mM) dATP, (0.2 mM) dGTP, (0.5 mM) dUTP, (1.4 mM) alpha thio-dCTP
6 mM Magnesium acetate
100 ug/ml BSA
1.82% Trehalose
360 uM DTT
2000 ng human DNA
1 Unit Uracil-N-glycosylase
5 Units Uracil-N-glycosylase Inhibitor
480 units BsoBI
30 units Bst
200 nM detector (GCIRSL.FD1 (SEQ ID NO: 31))
500 nM amplification primers (GCIRSL.APL1 (SEQ ID NO: 22) and GCIRSL.APR1 (SEQ ID NO: 24))
50 nM bumpers (GCIRSL.BL (SEQ ID NO: 27) and GCIRSL.BR (SEQ ID NO: 28))
100 ul reaction volume
Decontamination performed for 20 minutes at 45° C.
Amplification performed for 60 minutes at 52° C.

As explained in greater detail in the Examples, the sensitivity of GCIR5 and GCIRSL in fluorescent real time tSDA was assessed using the detectors GCIR5-FD10 (SEQ ID NO: 15) and GCIRSL-FD1 (SEQ ID NO: 31), with the plasmid GC10 as the target DNA source. The plasmid GC10 contains an 800 base pair region of the *Neisseria gonorrhoeae* genome inserted into pUC18. Fluorescent tSDA was performed using a titration of GC10 plasmid: 250, 100, 50, 25, and 12 copies. GCIR5 with FD10 was capable of detecting down to 25 copies of the GC10 plasmid. The sensitivity of GCIRSL in real time tSDA was determined to be at 250 copies of the GC10 plasmid. Judgement of a reaction being positive was determined by comparing the RFU values of sample reactions with those from negative controls (no target DNA added). If the reactions with GC10 produced RFU values greater than 2–3 times the average RFU values for the negative control, then it was considered positive.

Other detectors for GCIR5 had been tested in separate experiments: FD1 (SEQ ID NO: 21), FD2 (SEQ ID NO: 20), FD3 (SEQ ID NO: 17), FD6 (SEQ ID NO: 19), FD8 (SEQ ID NO: 16), and FD11 (SEQ ID NO: 18). While FD8, FD3, and FD1 were capable of detecting the GC10 plasmid at levels of 250 copies, others, such as FD11, FD6, and FD2, produced lower RFU values at this identical target concentration. This clearly demonstrates the importance of examining multiple detector sequences/lengths to achieve maximum sensitivity, and as a result, GCIR5-FD10 (SEQ ID NO: 15) was chosen as the primary detector to be used in real time fluorescent tSDA.

Specificity and crossreactivity of GCIR5 and GCIRSL were determined by testing various *Neisseria gonorrhoea* strains, other Neisseria species, and non-related bacteria and viruses. The 12 *Neisseria gonorrhoea* strains were tested at $1 \times 10^4$ genomes. All of the crossreactant DNAs were diluted to approximately $1 \times 10^7$ genomic copies. A summary of the specificity and crossreactivity from multiple experiments is seen in Table 5.

Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to the polymerase chain reaction (PCR), in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (α-thio dNTP), 3) nicking of a hemimodified double stranded restriction site, ) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. (1992, *Nuc. Acids Res.*, supra) and in U.S. Pat. No. 5,270,184 (hereby incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced form the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with Ugi prior to amplification of the target. Alternatively, UDG may be heat-inactivated. In thermophilic SDA, the higher temperature of the reaction itself ($\geq 50°$ C.) can be used to concurrently inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity is also of great importance, as it is nicking which perpetuates the reaction and allows subsequent rounds of target amplification to initiate.

Thermophilic SDA is performed essentially as the conventional SDA described by Walker, et al. (1992, *PNAS* and *Nuc. Acids Res.*, supra), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in thermophilic SDA are BsrI, BstNI, BsmAI, BslI and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ration of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

A detector oligonucleotide for homogeneous real time fluorescent tSDA is an oligonucleotide which comprises a single-stranded 5' or 3' section which hybridizes to the target sequence (the target binding sequence) and an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention for homogeneous real time fluorescent tSDA comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing in the secondary structure, it may include all or part of a first sequence involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target binding sequence of the detector oligonucleotide is present as a single-stranded 3' tail, the target binding sequence may also extend through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the secondary structure and the target binding sequence do not compromise the reaction. Perfect matches in the sequences involved in hybridization improve assay specificity without negative effects on reaction kinetics.

When added to the amplification reaction, the detector oligonucleotide signal primers of the invention are converted to double-stranded form by hybridization and extension of an amplification primer as described above. Strand displacement by the polymerase also unfolds or linearizes the secondary structure and converts it to double-stranded from by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as a) an increase in the ratio of donor fluorophore fluorescence after linearizing or unfolding the secondary structure and donor fluorophore fluorescence in the detector oligonucleotide prior to linearizing or unfolding, or b) as a decrease in the ration of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. As in SDA systems, linearization of the secondary structure and separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

The following Examples illustrate specific embodiments of the invention described herein. As would be apparent to skilled artisans, various changes and modifications are possible, and are contemplated within the scope of the invention described.

EXAMPLE 1

Design of tSDA Primer Sets

The 800 bp *N. gonorrhoeae* sequence identified was examined for the design of tSDA primer sets. Certain regions of the genome were avoided due to the presence of GC or AT stretches, and/or small repeats that would cause strong interactions between primers. The software program Oligo™ (National Biosciences, Inc., Plymouth, Minn.) was used to screen out tSDA sets that could potentially be problematic, due to primer/primer interactions with high-ΔG values. Various primer sets were designed within the region. Some sets were immediately dismissed and some were found to be lacking any serious interactions. Out of all the sets examined, one was chosen for further study—GCIR5. GCIR5 was designed with three variants of both the left and right amplification primers (FIG. 1). This allowed for the examination of various combinations of the primers, each of which had a different Tm. All of the primers encompassing the GCIR5 system and their positions can be seen in the diagram in FIG. 1.

EXAMPLE 2

Design of GCIR5 tSDA Reaction Conditions

A statistically designed experiment was performed to examine 5 out of 6 primer combinations of the GCIR5 primers in the presence of different co-solvent concentrations and amplification temperatures. This experiment was used to determine which primer pairings had the best capability of producing amplification across a wide spectrum of conditions. The following variables were examined: potassium phosphate (25 mM and 35 mM), DMSO (3% and 8%), glycerol (3.5% and 7%), human DNA (650 ng and 1050 ng), amplification temperature (52° C. and 54° C.). The results show that the following tSDA condition provided the greatest amplification:

Primers: GCIR5-AL5.3 (SEQ ID NO: 7)—0.5 μM
  GCIR-AR5.1 (SEQ ID NO: 8)—0.5 μM
  GCIR-BL5.1 (SEQ ID NO: 11)—0.05 μM
  GCIR-BR5.1 (SEQ ID NO: 12)—0.05 μM
Detectors: GCIR-D1L (SEQ ID NO: 13)—10 μM
Co-solvents: Potassium phosphate—35 nM
  DMSO—3%
  Glycerol—7%
  Magnesium acetate—5 mM
  DTT—0.36 mM
  Trehalose—1.82%
  BSA—100 μg/mL human DNA—650 ng
dNTPs—dCTP (1.4 mM), dUTP (0.5 mM), dGTP (0.2 mM), dATP (0.2 mM)
Enzymes: UDG—1 unit/50 μL reaction
UDI—5 units/50 μL reaction
BsoBI/Bst—160 units/9 units
Decontamination: 45° C. for 30 minutes
Amplification: 52° C. for 30 minutes Other primers such as GCIR-AL5.1 (SEQ ID NO: 5) would also be expected to be effective since all of the tested amplification primers were effective. Additionally, GCIR-D2L (SEQ ID NO: 14) could be used as a $^{32}P$ detector probe in place of D1L, or as a capture probe in an assay system. The combination of GCIR-AL5.3 and GCIR-AR5.1 was found to be the optimal primer set. All of the primer sets tested were able to amplify N. gonorrhoeae BDMS 2900 at $1 \times 10^6$ genomes, although some sets were more effective than others under certain conditions. Further experimentation with these primer sets based on strategic design resulted in optimization of the above reaction conditions by changing the DMSO and glycerol concentrations to 5.5% DMSO and 5.2% glycerol. All other co-solvents and enzyme concentrations were identical to those above.

EXAMPLE 3

Assay of GCIR5 tSDA Sensitivity

Utilizing the optimal tSDA conditions described in Example 2, a limit of detection experiment was set up. A titration of N. gonorrhoeae strain BDMS 2900 from $1 \times 10^6$ down to 1 genome/reaction was performed. The titration panel was tested with the GCIR5 tSDA system in the presence of human DNA at 650 ng and 1250 ng/reaction. Single samples of $1 \times 10^6$, $1 \times 10^5$ and $1 \times 10^4$ genomes/reaction were tested, $1 \times 10^3$ genomes/reaction was tested in duplicate, and 100, 10 and 1 genomes were tested in triplicate. A negative control was also included in the experiment. The method of testing low copy numbers of the N. gonorrhoeae genome in multiple reactions was done to ensure that the lack of amplification in one sample was not considered to be indicative of the system's sensitivity, since sampling error could cause such a result. The result of the sensitivity experiment is that GCIR5 was capable of detecting down to 10 genomes/reaction three out of three times and 1 genome/reaction 1 out of three times.

EXAMPLE 4

Assay of N. gonorrhoeae tSDA Specificity and Crossreactivity

Experiments were set up to examine the specificity and crossreactivity of the GCIR5 tSDA system. The optimal primer set described in Example 2 was utilized in this experiment. Several strains of N. gonorrhoeae were tested at $1 \times 10^6$ genomes/reaction. GCIR5 was capable of amplifying every one of the tested strains listed in Table 2. This tSDA system's specificity was satisfactory. It was next determined whether there would be any crossreactivity with any of the other Neisseria species or non Neisseria bacteria. To accomplish this, all of the non-crossreactant bacteria were tested at a level of $1 \times 10^7$ genomes/reaction. In none of the reactions was any amplification product detected (Table 3).

TABLE 2

| Organism | Strain | GCIR5 | GCIRSL | GC O2 |
| --- | --- | --- | --- | --- |
| Negative Control | 50 ng human DNA | – | – | – |
| Neisseria gonorrhoeae | CDC111 | + | + | + |
| Neisseria gonorrhoeae | BDMS 1632 | + | + | + |
| Neisseria gonorrhoeae | ATCC 19424 | + | + | + |
| Neisseria gonorrhoeae | BDMS 2900 | + | + | + |
| Neisseria gonorrhoeae | ATCC 35201 | + | + | + |
| Neisseria gonorrhoeae | ATCC 35541 | + | + | + |
| Neisseria gonorrhoeae | ATCC 35542 | + | + | + |
| Neisseria gonorrhoeae | ATCC 43069 | + | + | + |
| Neisseria gonorrhoeae | ATCC 43070 | + | + | + |
| Neisseria gonorrhoeae | BDMS 454 | + | + | + |
| Neisseria gonorrhoeae | ATCC 49226 | + | + | + |
| Neisseria gonorrhoeae | ATCC 51109 | + | + | not tested |

TABLE 3

| Organism | Strain | GCIR 5 | GCIRSL | GC O2 |
| --- | --- | --- | --- | --- |
| Negative Control | 50 ng hDNA | — | — | — |
| Neisseria meningitidis | ATCC 13090 | not tested | — | — |
| Neisseria meningitidis | ATCC 14632 | — | — | — |
| Neisseria meningitidis | ATCC 13077 | — | — | — |
| Neisseria meningitidis | ATCC 13102 GRP C | — | — | — |
| Neisseria meningitidis | ATCC 13113 GRP D | — | — | — |
| Neisseria meningitidis | ATCC 35559 GRP W-135 | — | — | — |
| Neisseria lactamica | ATCC 44418 | — | — | — |
| Neisseria lactamica | ATCC 49142 | — | — | — |
| Neisseria lactamica | ATCC 23970 | — | — | — |
| Neisseria lactamica | ATCC 23971 | — | — | — |
| Neisseria lactamica | ATCC 23972 | — | — | — |
| Chlamydiae trachomatis | L2 | — | — | — |
| Chlamydiae trachomatis | J | — | — | — |
| Chlamydiae psittaci | | — | — | — |
| Chlamydiae pneumoniae | | — | — | — |
| Neisseria flavescens | ATCC 13120 | — | — | — |
| Neisseria sicca | ATCC 29193 | — | — | — |
| Neisseria sicca | ATCC 9913 | — | — | — |
| Neisseria subflava | ATCC 14799 | — | — | — |
| Neisseria subflava | ATCC 19243 | — | not tested | — |
| Neisseria cinerea | ATCC 14685 | — | — | — |
| Neisseria elongata | ATCC 25295 | — | — | — |

TABLE 3-continued

| Organism | Strain | GCIR 5 | GCIRSL | GC O2 |
|---|---|---|---|---|
| Neisseria mucosa | ATCC 19696 | — | — | — |
| Branhamella catarrhalis | ATCC 25240 | — | — | — |
| Moraxella lacunata | ATCC 17967 | — | — | — |
| Kingella kingae | ATCC 23330 | — | — | — |
| Salmonella typhimurium | ATCC 13311 | — | — | — |
| Salmonella minnesota | ATCC 9700 | — | — | — |
| Staph aureus | ATCC 12598 | — | — | — |
| Acinetobacter lwoffi | ATCC 19001 | — | — | — |
| E. coli | ATCC 11775 | — | — | — |
| Klebsiella pneumoniae | ATCC 13883 | — | — | — |
| Gardnerella vaginalis | ATCC 14018 | — | — | — |
| Streptococcus Group A | ATCC 16915 | — | — | — |
| Streptococcus Group B | ATCC 12386 | — | — | — |
| Proteus mirabilis | ATCC 29906 | — | — | — |
| Haemophilus influenzae b | ATCC 33533 | — | — | — |
| Mycoplasma orale | ATCC 23714 | — | — | — |
| HSV-1 | McINTYRE | — | — | — |
| HSV-2 | Strain G | — | — | — |
| Trichomonas vaginalis | ATCC 30001 | — | — | — |
| Candida albicans | ATCC 44808 | — | — | — |
| Streptococcus faecalis | ATCC 29212 | — | — | — |
| Peptostreptococcus productus | ATCC 27340 | — | — | — |

EXAMPLE 5

GCIR5 Primers in Fluorescent Real Time tSDA

Assays for *Neisseria gonorrhoeae* were performed using fluorescent real time tSDA. The primers, bumpers and detectors designed for this are shown in FIG. 1. The sensitivity and crossreactivity of GCIR5 with detector FD1 (SEQ ID NO: 21) was assayed (Table 4). A plasmid (GC10) that contains an 800 base pair region of the *Neisseria gonorrhoeae* genome inserted into pUC18 was used as the target. The testing was conducted with from 1000 to 25 copies of the plasmid. The conditions of the tSDA were:

5.2% Glycerol
5.5% DMSO
35 mM potassium phosphate
2000 ng human DNA
320 units BsoB1
20 units Bst
200 NM detector (FD1)
500 nM amplification primers (AL5.3 (SEQ ID NO: 7) and AR5.1 (SEQ ID NO: 8))
50 nM bumpers (BL5.1 (SEQ ID NO: 11) and BR5.1 (SEQ ID NO: 12))
Decontamination was performed for 20 minutes at 45° C.
Amplification was performed for 60 minutes at 52° C.

A PerSeptive Biosystems CytoFluor Series 4000 Multi-well plate reader ("the PerSeptive Instrument") was used. Reactions of 100 μL volume were transferred into Lab Systems Microtiter Strips. The sensitivity of GCIR5 with FD1 is in the range of 50 copies of the cloned *Neisseria gonorrhoeae* DNA in GC10. Table 4 lists all of the cross-reactants tested with GCIR5-FD1. Each of these crossreactants was tested at $5 \times 10^7$ genomes (Table 4). Certain *N. menngitidis* and *N. lactamica* strains produced fluorescence over time. These results indicate a problem with crossreactivity and make the GCIR5-FD1 combination an unlikely candidate for a useful assay system using fluorescent real time tSDA.

TABLE 4

| Organism | Strain | GCIR5-FD1 | GCIR5-FD3 | GCIR5-FD8 | GCIR5-FD10 |
|---|---|---|---|---|---|
| Chlamydia trachomatis | J | – | NT | – | – |
| Chlamydia trachomatis | LGV II | – | NT | – | – |
| Chlamydia psittaci | | – | NT | – | – |
| Chlamydia pneumoniae | | – | NT | – | – |
| Neisseria meningitidis | ATCC 14632 | – | – | – | – |
| Neisseria meningitidis | ATCC 13077 | – | – | – | – |
| Neisseria meningitidis | ATCC 13102 | – | – | – | – |
| Neisseria meningitidis | ATCC 13113 | – | NT | – | – |
| Neisseria meningitidis | ATCC 35559 | – | NT | – | – |
| Neisseria meningitidis | ATCC 13090 | + | Wk | Wk | Wk |
| Neisseria lactamica | ATCC 23971 | + | Wk | Wk | Wk |
| Neisseria lactamica | ATCC 44418 | – | – | – | – |
| Neisseria lactamica | ATCC 49142 | + | Wk | Wk | Wk |
| Neisseria lactamica | ATCC 23970 | – | – | – | – |
| Neisseria lactamica | ATCC 23972 | + | Wk | Wk | Wk |
| Neisseria flavescens | ATCC 13120 | – | NT | – | – |
| Neisseria sicca | ATCC 29193 | – | NT | – | – |
| Neisseria subflava | ATCC 14799 | – | NT | – | – |
| Neisseria cinerea | ATCC 14685 | – | NT | – | – |
| Neisseria elongata | ATCC 25295 | – | NT | – | – |
| Neisseria mucosa | ATCC 19696 | – | NT | – | – |
| Branhamella catarrhalis | ATCC 25240 | – | NT | – | – |
| Moraxella lacunata | ATCC 17967 | – | NT | – | – |

TABLE 4-continued

| Organism | Strain | GCIR5-FD1 | GCIR5-FD3 | GCIR5-FD8 | GCIR5-FD10 |
|---|---|---|---|---|---|
| Kingella kingae | ATCC 23330 | – | NT | – | – |
| Salmonella typhimurium | ATCC 13311 | – | NT | – | – |
| Salmonella minnesota | ATCC 9700 | – | NT | – | – |
| Staphylococcus aureus | ATCC 12598 | – | NT | – | – |
| Acinetobacter lwoffi | ATCC 19001 | – | NT | – | – |
| E. coli | ATCC 11775 | – | NT | – | – |
| Klebsielia pneumoniae | ATCC 13883 | – | NT | – | – |
| Gardnerella vaginalis | ATCC 14018 | – | NT | – | – |
| Streptococcus Group A | ATCC 16915 | – | NT | – | – |
| Streptococcus Group B | ATCC 12386 | – | NT | – | – |
| Proteus mirabilis | ATCC 29906 | – | NT | – | – |
| Haemophilus influenzae B | ATCC 33533 | – | NT | – | – |
| Mycoplasma orale | ATCC 23714 | – | NT | – | – |
| HSV-1 | McINTYRE | – | NT | – | – |
| HSV-2 | Strain G | – | NT | – | – |
| Trichomonas vaginalis | ATCC 30001 | – | NT | – | – |
| Candida albicans | ATCC 44808 | – | NT | – | – |
| Streptococcus faecalis | ATCC 29212 | – | NT | – | – |
| Peptostreptococcus productus | ATCC 27340 | – | NT | – | – |

+ Positive
– Negative
Wk Weakly Positive
NT Not Tested

EXAMPLE 6

Sensitivity of GCIR5 with Detectors FD8 and FD10 in a Fluorescent Real Time tSDA Assay The sensitivity of GCIR5 in fluorescent real time tSDA was assessed using detector probes FD8 (SEQ ID NO: 16) and FD10 (SEQ ID NO: 15). These two detector probes are shown in FIG. 1. Plasmid GC10 was used as the target. The conditions for the tSDA reaction were as follows:
5.2% Glycerol
5.5% DMSO
35 mM potassium phosphate
2000 ng Human DNA
320 units BsoB1
20 Units Bst
200 nM detector FD8 or FD10
500 nM amplification primers AL5.3 (SEQ ID NO: 7) and AR 5.1 (SEQ ID NO: 8)
50 nM Bumpers BL5.1 (SEQ ID NO: 11) and BR5.1 (SEQ ID NO: 12)
Decontamination was for 20 minutes at 45° C.
Amplification was for 60 minutes at 52° C.

The PerSeptive Instrument was used for these assays. Labsystems Microtiter Plate Strips were used with the PerSeptive Instrument. The volume of the reactions was 100 µL. Both GCIR5-FD8 and GCIR5-FD10 combinations were capable of detecting down to 12 copies of the GC10 plasmid. This data is shown in Table 5. RFU values 2–3 times above background are considered positive.

TABLE 5

| Target | FD10 RFU | FD8 RFU |
|---|---|---|
| 100 | 573 | 631 |
|  | 734 | 716 |
| 50 | 274 | 1256 |
|  | 400 | 412 |
|  |  | 585 |
| 25 | 142 | 168 |
|  | 213 | 249 |
|  |  | 283 |
| 12.5 | 247 | 254 |
|  | 126 | 210 |
|  | 133 | 321 |
| 0 | 119 | 103 |
|  | 116 | 120 |

EXAMPLE 7

Assay of Crossreactivity of GCIR5 with Detectors FD3, FD8 or FD10 in Real Time Fluorescent tSDA The crossreactivity of GCIR5 in combination with any one of detectors FD3 (SEQ ID NO: 17), FD8 (SEQ ID NO: 16) or FD10 (SEQ ID NO: 15) was assayed in real time fluorescent tSDA. These three detector probes are shown in FIG. 1. In Example 5 it was shown that GCIR5 in combination with FD1 (SEQ ID NO: 21) did show crossreactivity with specific N. meningitidis and lactamica strains. tSDA was performed using the target plasmid GC10. A positive control of 250 copies was tested for all of the fluorescent detectors. A negative control was also tested. Neisseria meningitidis ATCC 13090, Neisseria lactamica ATCC 23971, 23972 and 49142 were all tested at $1 \times 10^7$ genomic copies. The tSDA conditions used were as follows:
5.2% Glycerol
5.5% DMSO
35 mM potassium phosphate
2500 ng Human DNA
320 Units BsoB1
20 Units Bst
167 Detector (either FD3, FD8 or FD 10)
500 nM Amplification Primers (AL5.3 (SEQ ID NO: 7) and AR5.1 (SEQ ID NO: 8))
50 nM Bumpers (BL5.1 (SEQ ID NO: 11) and BR5.1 (SEQ ID NO: 12))
Decontamination was for 20 minutes at 45° C.
Amplification was for 60 minutes at 52° C.

The PerSeptive Instrument was used for these assays. Reactions of 100 µL were transferred into Lab Systems Microtiter Strips. None of the assays using FD3, FD8 or FD10 showed significant crossreactivity with the tested strains. These detectors all produced positive result for the 250 copies of GC10. To the contrary, detectors FD11 (SEQ ID NO: 18) and FD6 (SEQ ID NO: 19) yielded results showing that these detectors in combination with the primers and bumper used will not give useful results. FD11 showed some crossreactivity while FD6 failed to show positive results even with the control target. These results are shown in Table 6. The FD3 detector probe assays were conducted in duplicate.

TABLE 6

| Target | FD3 RFU | FD8 RFU | FD11 RFU | FD3 RFU | FD6 RFU | FD10 RFU |
|--------|---------|---------|----------|---------|---------|----------|
| 0      | 109     | 120     | 148      | 123     | 127     | 131      |
|        | 135     | 117     | 183      | 127     | 125     | 131      |
| 250    | 591     | 876     | 276      | 312     | 126     | 899      |
|        | 586     | 801     | 182      | 374     | 121     | 803      |
| NM90   | 150     | 128     | 217      | 217     | 119     | 139      |
|        | 145     | 147     | 210      | 125     | 121     | 136      |
| NL42   | 137     | 143     | 196      | 127     | 170     | 128      |
|        | 125     | 127     | 208      | 133     | 159     | 130      |
| NL71   | 125     | 131     | 172      | 126     | 127     | 128      |
|        | 126     | 137     | 215      | 121     | 133     | 131      |
| NL72   | 141     | 134     | 172      | 119     | 150     | 131      |
|        | 134     | 28      | 186      | 121     | 147     | 128      |

EXAMPLE 8

Sensitivity of GCIR5 with FD8 or FD10 in Real Time Fluorescent tSDA Assays

To assay the sensitivity of GCIR5-FD8 (SEQ ID NO: 16) and GCIR5-FD10 (SEQ ID NO: 15) systems in real time fluorescent tSDA assays, a titration of GC10 plasmid from 250 to 6.25 copies was performed. Each titration concentration was tested in triplicate to assure sensitivity. The tSDA conditions used were the same as in Example 7.

A PerSeptive Instrument was used for the assays. Reaction volumes of 100 $\mu$L were transferred into Lab Systems Microtiter Strips. The results are shown in Table 7. The sensitivity of GCIR5 with FD8 and FD10 is in the range of 12 to 25 copies of cloned *Neisseria gonorrhoeae* DNA. The RFU values for 25 copies of GC10 are all well above the background values seen in the negative controls. The sensitivity at 12.5 copies of GC10 begins to wane. In some samples reactions appear positive while others remain at a background level of fluorescence.

TABLE 7

| Copies GC10 | FD8 Final RFU | FD10 Final RFU |
|-------------|---------------|----------------|
| 250         | 1076          | 524            |
| 100         | 479           | 889            |
|             | 992           | 702            |
|             | 468           | 490            |
| 50          | 382           | 215            |
|             | 694           | 364            |
|             | 613           | 702            |
| 25          | 599           | 484            |
|             | 573           | 479            |
|             | 751           | 656            |
| 12.5        | 116           | 126            |
|             | 305           | 111            |
|             | 255           | 215            |
| 6.25        | 139           | 330            |
|             | 98            | 111            |
|             | 131           | 137            |
| Negatives   | 99            | 118            |
|             | 94            | 130            |
|             | 101           | 119            |

EXAMPLE 9

Primer Screen for GCIRSL tSDA

Whereas Examples 2–5 were directed to experiments performed with GCIR5, this Example as well as the following Examples (6–8) are directed to results obtained using GCIRSL. A statistically designed experiment was performed to evaluate the best primer pair from all the different primer combinations (FIG. 2) for GCIRSL. The design tested two levels of each for potassium phosphate (25 mM and 35 mM), hDNA (500 ng and 1200 ng), temperature (52° C. and 54° C.), glycerol (3% and 7%) and DMSO (3% and 7%). All primer combinations amplified $10^6$ genomes per reaction of *Neisseria gonorrhoeae* strain BDMS 2900. The primer combination that showed the best amplification over the widest range of conditions was GCIRSL.APL1 (SEQ ID NO: 22)/GCIRSL APR3 (SEQ ID NO: 26). The condition that demonstrated the greatest amplification was chosen for the sensitivity, specificity and crossreactivity experiments and is listed below.

tSDA reaction conditions for GCIRSL (50 $\mu$L)
25 mM Potassium phosphate pH 7.6
7% Glycerol
3% DMSO
6 mM Magnesium acetate
500 ng hDNA
100 $\mu$g/mL acetylated BSA
360 $\mu$M DTT
0.5 mM dUTP
0.2 mM dATP
0.2 mM dGTP
0.2 mM $\alpha$-thio-dCTP
0.5 $\mu$M tSDA primers
0.05 $\mu$M tSDA bumpers
160 Units of BsoB1
9 Units of Bst polymerase
1 Unit Uracil-N-glycosylase
5 Units Uracil-N-glycosylase Inhibitor
1.82% Trehalose
Decontamination at 45° C. for 30 minutes
Amplification at 54° C. for 60 minutes

EXAMPLE 10

Assay of GCIRSL tSDA Sensitivity

A genome titration was performed on *N. gonorrhoeae* strain BDMS 2900 to determine the minimum number of genomes that could be amplified and detected in tSDA. *N. gonorrhoeae* DNA was isolated and diluted in 10 ng/$\mu$L human placental DNA. tSDA reactions were performed using $10^5$, $10^4$, $10^3$, $10^2$, 10, 1 and 0 genomes per reaction. The limit of detection for GCIRSL was 10 genomes per reaction.

EXAMPLE 11

Assay of GCIRSL tSDA Specificity

The specificity of the GCIRSL system was tested using 12 *Neisseria gonorrhoeae* strains at $10^6$ genomes per reaction. All 12 *Neisseria gonorrhoeae* strains were detected. Results are summarized in Table 2 above.

EXAMPLE 12

Assay of GCIRSL tSDA Crossreactivity

Crossreactivity experiments were performed on 43 Neisseria and non-Neisseria species at $10^7$ genomes per reaction. No crossreactivity was seen with any of the 43 crossreactants tested. Results are summarized in Table 3 above.

EXAMPLE 13

GCIRSL Primers in Fluorescent Real time tSDA

Assays for *Neisseria gonorrhoeae* were performed using fluorescent real time tSDA. The primers, bumpers and detectors designed for this are shown in FIG. 2. The sensitivity of GCIRSL with detector FD1 (SEQ ID NO: 31) was assayed. GC10 was used as the target, being tested from 500 to 25 copies of the plasmid. The conditions of the tSDA were:
35 mM Potassium phosphate pH7.6
7% Glycerol
7% DMSO
6 mM MgAc
1450 ng λDNA
100 ug/ml acetylated BSA
360 mM DTT
0.5 mM dUTP and 0.2 m dATP, dGTP, and 1.4 mM alpha thio-dCTP
0.5 uM and 0.05 uM of tSDA primers (APL1 (SEQ ID NO: 22) and APR3 (SEQ ID NO: 26) and bumpers (BL (SEQ ID NO: 27) and BR (SEQ ID NO: 28)), respectively
100 nM detector (FD1)
480 Units of BsoB1
30 Units of Bst
Decontamination was performed for 20 minutes at 45° C.
Amplification was performed for 60 minutes at 52° C.

The "PerSeptive Instrument" was used. Reactions of 100 ul volume were transferred into Lab Systems Microtiter Strips. The results are shown in Table 8. The sensitivity of GCIRSL with FD1 is in the range of 100 copies of the cloned *Neisseria gonorrhoeae* plasmid GC 10.

TABLE 8

| Copies GC10 | Final RFU |
| --- | --- |
| 500 | 506 |
|  | 308 |
|  | 390 |
| 250 | 345 |
|  | 318 |
|  | 192 |
| 100 | 135 |
|  | 201 |
|  | 217 |
| 50 | 205 |
|  | 109 |
| 25 | 172 |
|  | 157 |
|  | 147 |
| 0 | 93 |
|  | 89 |
|  | 89 |

EXAMPLE 14 tSDA Primer Evaluation of GC O2

Besides the GCIR5 and GCIRSL sets of primers, a third set of primers, GC O2, was also examined. A strategically designed experiment was performed to test all possible primer combinations of the two left end and two right end primers. The following variables were used: potassium phosphate (25 mM and 35 mM), glycerol (3.1% and 8%), DMSO (3% and 8%) and temperature (52° C. and 54° C.). All of the primer sets amplified $10^6$ genomes of GC 35201. The most robust primer combination chosen for further experiments was O2AL42.1 (SEQ ID NO: 33) and O2AR42.1 (SEQ ID NO: 35). The most sensitive detector probe is O2DL42.1 (SEQ ID NO: 38), which was used for further experiments. The conditions chosen to test sensitivity, specificity and crossreactivity are listed below:
tSDA reaction mixture
35 mM Potassium phosphate, pH 7.6
8% Glycerol
3% DMSO
6 mM Magnesium acetate
650 ng human placental DNA
1.4 mM thio-dCTP
0.5 mM dUTP
0.2 mM dATP
0.2 mM dGTP
9 units Bst polymerase
16 units BsoB1 restriction enzyme
1 unit uracil-N-glycosylase
2 units uracil-N-glycosylase inhibitor
0.5 μM tSDA primers
0.05 μM tSDA bumpers 02BL42.1 (SEQ ID NO: 36) and 02BR42.1 (SEQ ID NO: 37)
1.82% trehalose
0.36 mM dithiothreitol
100 μg/mL acetylated bovine serum albumin
0.015% antifoam
Decontamination was at 45° C. for 30 minutes
Amplification was at 52° C. for 60 minutes

EXAMPLE 15

Assay of GC O2 tSDA Sensitivity

A genome titration was performed to determine the minimum genome copy number of GC strain BDMS 2900 amplified and detected in the GC O2 tSDA system. GC genomic DNA was isolated and diluted in human placental DNA. tSDA reactions were performed using $10^4$, $10^3$, $10^2$, 10, 1 and 0 genome copies per reaction. A sensitivity of 100 genome copies was achieved for the GC O2 system.

EXAMPLE 16

Assay of GC O2 tSDA Specificity

The specificity of the GC O2 system was tested using 11 *Neisseria gonorrhoeae* strains at $10^6$ genomes per reaction. All 11 strains were detected as shown in Table 2 above.

EXAMPLE 17

Assay of GC O2 tSDA Crossreactivity

The crossreactivity of the GC O2 system was tested with 44 related bacterial species at $10^7$ genomes per reaction. No crossreactant species were detected as shown in Table 3 above.

While the invention has been described with some specificity, modifications apparent to those with ordinary skill in the art may be made without departing from the scope of the invention. Various features of the invention are set forth in the following claims.

What is claimed is:

1. A nucleic acid selected from the group consisting of GCIR-AL5.1 (SEQ ID NO: 5), GCIR-AL5.2 (SEQ ID NO: 6) and GCIR-AL5.3 (SEQ ID NO: 7).

2. A nucleic acid selected from the group consisting of GCIR-AR5.1 (SEQ ID NO: 8), GCIR-AR5.2 (SEQ ID NO: 9) and GCIR-AR5.3 (SEQ ID NO: 10).

3. A nucleic acid selected from the group consisting of GCIR-BL5.1 (SEQ ID NO: 11) and GCIR-BR5.1 (SEQ ID NO: 12).

4. A nucleic acid selected from the group consisting of GCIR-D1L (SEQ ID NO: 13), a complementary nucleic acid of SEQ ID NO: 13, GCIR-D2L (SEQ ID NO: 14) and a complementary nucleic acid of SEQ ID NO: 14.

5. The nucleic acid of claim 4 wherein said nucleic acid comprises a detectable marker.

6. The nucleic acid of claim 5 wherein said detectable marker is selected from the group consisting of a radioactive marker and a fluorescence marker.

7. A nucleic acid selected from the group consisting of GCIR5-FD3 (SEQ ID NO: 17), a complementary nucleic acid of SEQ ID NO: 17, GCIR5-FD8 (SEQ ID NO: 16), a complementary nucleic acid of SEQ ID NO: 16, GCIR5-FD10 (SEQ ID NO: 15), a complementary nucleic acid of SEQ ID NO: 15, GCIR5-FD11 (SEQ ID NO: 18), a nucleic acid complementary to SEQ ID NO: 18, GCIR5-FD6 (SEQ ID NO: 19), a nucleic acid complementary to SEQ ID NO: 19, GCIR5-FD2 (SEQ ID NO: 20), a nucleic acid complementary to SEQ ID NO: 20, GCIR5-FD1 (SEQ ID NO: 21) and a nucleic acid complementary to SEQ ID NO: 21.

8. The nucleic acid of claim 7 wherein said nucleic acid comprises a detectable marker.

9. The nucleic acid of claim 8 wherein said detectable marker is a fluorescence marker.

10. A nucleic acid selected from the group consisting of GCIRSL.APL1 (SEQ ID NO: 22) and GCIRSL.APL2 (SEQ ID NO: 23).

11. A nucleic acid selected from the group consisting of GCIRSL-APR1 (SEQ ID NO: 24), GCIRSL-APR2 (SEQ ID NO: 25) and GCIRSL-APR3 (SEQ ID NO: 26).

12. A nucleic acid selected from the group consisting of GCIRSL-BL (SEQ ID NO: 27) and GCIRSL-BR (SEQ ID NO: 28).

13. A nucleic acid selected from the group consisting of GCIRSL-DL1 (SEQ ID NO: 29), a complementary nucleic acid of SEQ ID NO: 29, GCIRSL-DL2 (SEQ ID NO: 30) and a complementary nucleic acid of SEQ ID NO: 30.

14. The nucleic acid of claim 13 wherein said nucleic acid comprises a detectable marker.

15. The nucleic acid of claim 14 wherein said detectable marker is selected from the group consisting of a radioactive marker and a fluorescence marker.

16. A nucleic acid selected from the group consisting of GCIRSL.FD1 (SEQ ID NO: 31) and a nucleic acid complementary to SEQ ID NO: 31.

17. The nucleic acid of claim 16 comprising a detectable marker.

18. The nucleic acid of claim 17 wherein said detectable marker is a fluorescence marker.

19. A nucleic acid selected from the group consisting of O2AL44.1 (SEQ ID NO: 32) and O2AL42.1 (SEQ ID NO: 33).

20. A nucleic acid selected from the group consisting of O2AR46.1 (SEQ ID NO: 34) and O2AR42.1 (SEQ ID NO: 35).

21. A nucleic acid selected from the group consisting of O2BL42.1 (SEQ ID NO: 36) and O2BR42.1 (SEQ ID NO: 37).

22. A nucleic acid selected from the group consisting of O2DL42.1 (SEQ ID NO: 38), a complementary nucleic acid of SEQ ID NO: 38, O2DR42.1 (SEQ ID NO: 39) and a complementary nucleic acid of SEQ ID NO: 39.

23. The nucleic acid of claim 22 wherein said nucleic acid comprises a detectable marker.

24. The nucleic acid of claim 23 wherein said detectable marker is selected from the group consisting of a radioactive marker and a fluorescence marker.

25. A nucleic acid selected from the group consisting of GC1.3 (SEQ ID NO: 1), GC2.3 (SEQ ID NO: 2), IR.R2 (SEQ ID NO: 3) and IRL1 (SEQ ID NO: 4).

26. A kit comprising:
   a) one or more primers selected from the group consisting of GCIR-AL5.1 (SEQ ID NO: 5), GCIR-AL5.2 (SEQ ID NO: 6) and GCIR-AL5.3 (SEQ ID NO: 7),
   b) one or more primers selected from the group consisting of GCIR-AR5.1 (SEQ ID NO: 8), GCIR-AR5.2 (SEQ ID NO: 9) and GCIR-AR5.3 (SEQ ID NO: 10),
   c) bumpers GCIR-BL5.1 (SEQ ID NO: 11) and GCIR-BR5.1 (SEQ ID NO: 12), and
   d) one or more detectors selected from the group consisting of GCIR-D1L (SEQ ID NO: 13), a nucleic acid complementary to SEQ ID NO: 13, GCIR-D2L (SEQ ID NO: 14), a nucleic acid complementary to SEQ ID NO: 14, GCIR5-FD3 (SEQ ID NO: 17), a complementary nucleic acid of SEQ ID NO: 17, GCIR5-FD8 (SEQ ID NO:16), a complementary nucleic acid of SEQ ID NO: 16, GCIR5-FD10 (SEQ ID NO: 15), a complementary nucleic acid of SEQ ID NO: 15, GCIR5-FD11 (SEQ ID NO: 18), a nucleic acid complementary to SEQ ID NO: 18, GCIR5-FD6 (SEQ ID NO: 19), a nucleic acid complementary to SEQ ID NO: 19, GCIR5-FD2 (SEQ ID NO: 20), a nucleic acid complementary to SEQ ID NO: 20, GCIR5-FD1 (SEQ ID NO: 21) and a nucleic acid complementary to SEQ ID NO: 21.

27. The kit of claim 26 wherein said detector comprises a detectable marker.

28. A kit comprising:
   a) one or more primers selected from the group consisting of GCIRSL-APL1 (SEQ ID NO: 22) and GCIRSL-APL2 (SEQ ID NO: 23),
   b) one or more primers selected from the group consisting of GCIRSL-APR1 (SEQ ID NO: 24), GCIRSL-APR2 (SEQ ID NO: 25) and GCIRSL-APR3 (SEQ ID NO: 26),
   c) bumpers GCIRSL-BL (SEQ ID NO: 27) and GCIRSL-BR (SEQ ID NO: 28), and
   d) one or more detectors selected from the group consisting of GCIRSL-DL1 (SEQ ID NO: 29), a nucleic acid complementary to SEQ ID NO: 29, GCIRSL-DL2 (SEQ ID NO: 30), a nucleic acid complementary to SEQ ID NO: 30, GCIRSL.FD1 (SEQ ID NO: 31) and a nucleic acid complementary to SEQ ID NO: 31.

29. The kit of claim 28 wherein said detector comprises a detectable marker.

30. A kit comprising:
   a) one or more primers selected from the group consisting of O2AL44.1 (SEQ ID NO: 32) and O2AL42.1 (SEQ ID NO: 33),
   b) one or more primers selected from the group consisting of O2AR46.1 (SEQ ID NO: 34) and O2AR42.1 (SEQ ID NO: 35),
   c) bumpers O2BL42.1 (SEQ ID NO: 36) and O2BR42.1 (SEQ ID NO: 37), and
   d) one or more detectors selected from the group consisting of O2DL42.1 (SEQ ID NO: 38), a nucleic acid complementary to SEQ ID NO: 38, O2DR42.1 (SEQ ID NO: 39) and a nucleic acid complementary to SEQ ID NO: 39.

31. The kit of claim 30 wherein said detector comprises a detectable marker.

32. A kit comprising:
   a) primers GCIR-AL5.3 (SEQ ID NO: 7) and GCIR-AR5.1 (SEQ ID NO: 8),
   b) bumpers GCIR-BL5.1 (SEQ ID NO: 11) and GCIR-BR5.1 (SEQ ID NO: 12), and
   c) one or more detectors selected from the group consisting of GCIR5-FD10 (SEQ ID NO: 15) and a nucleic acid complementary to SEQ ID NO: 15.

33. The kit of claim 32 wherein said detector comprises a fluorescence marker.

34. A method for detecting the presence or absence of *Neisseria gonorrhoeae* in a sample, said method comprising the steps of:
   a) treating said sample using a pair of nucleic acid primers in a nucleic acid amplification reaction wherein a first primer is selected from the group consisting of GCIR-AL5.1 (SEQ ID NO: 5), GCIR-AL5.2 (SEQ ID NO: 6) and GCIR-AL5.3 (SEQ ID NO: 7) and a second primer is selected from the group consisting of GCIR-AR5.1 (SEQ ID NO: 8), GCIR-AR5.2 (SEQ ID NO: 9) and GCIR-AR5.3 (SEQ ID NO: 10), and
   b) detecting any amplified nucleic acid product,
   wherein detection of amplified product indicates the presence of *Neisseria gonorrhoeae*.

35. The method of claim 34 wherein said nucleic acid amplification reaction is a Strand Displacement Amplification (SDA) reaction.

36. The method of claim 35 wherein said SDA reaction utilizes GCIR-BL5.1 (SEQ ID NO: 11) and GCIR-BR5.1 (SEQ ID NO: 12) as bumpers.

37. The method of claim 34 wherein detecting said amplified nucleic acid product is conducted by hybridizing said amplified nucleic acid product with a detector selected from the group consisting of GCIR-D1L (SEQ ID NO: 13), a complementary nucleic acid of SEQ ID NO: 13, GCIR-D2L (SEQ ID NO: 14), a complementary nucleic acid of SEQ ID NO: 14, GCIR5-FD3 (SEQ ID NO: 17), a complementary nucleic acid of SEQ ID NO: 17, GCIR5-FD8 (SEQ ID NO: 16), a complementary nucleic acid of SEQ ID NO: 16; GCIR5-FD10 (SEQ ID NO: 15), a complementary nucleic acid of SEQ ID NO: 15, GCIR5-FD11 (SEQ ID NO: 18), a nucleic acid complementary to SEQ ID NO: 18, GCIR5-FD6 (SEQ ID NO: 19), a nucleic acid complementary to SEQ ID NO: 19, GCIR5-FD2 (SEQ ID NO: 20), a nucleic acid complementary to SEQ ID NO: 20, GCIR5-FD1 (SEQ ID NO: 21) and a nucleic acid complementary to SEQ ID NO: 21.

38. The method of claim 35 wherein said SDA reaction is a thermal Strand Displacement Amplification (tSDA) reaction.

39. The method of claim 38 wherein said tSDA reaction is a homogeneous fluorescent real time tSDA reaction.

40. The method of claim 39 wherein said homogeneous fluorescent real time tSDA reaction utilizes GCIR-BL5.1 (SEQ ID NO: 11) and GCIR-BR5.1 (SEQ ID NO: 12) as bumpers.

41. The method of claim 40 wherein said first primer is GCIR-AL5.3 (SEQ ID NO: 7) and said second primer is GCIR-AR5.1 (SEQ ID NO: 8).

42. The method of claim 41 wherein detecting said amplified nucleic acid product is conducted by hybridizing said amplified nucleic acid product with detector GCIR5-FD10 (SEQ ID NO: 15).

43. A method for detecting the presence or absence of *Neisseria gonorrhoeae* in a sample, said method comprising the steps of:

a) treating said sample using a pair of nucleic acid primers in a nucleic acid amplification reaction wherein a first primer is selected from the group consisting of GCIRSL-APL1 (SEQ ID NO: 22), and GCIRSL-APL2 (SEQ ID NO: 23) and a second primer is selected from the group consisting of GCIRSL-APR1 (SEQ ID NO: 24), GCIRSL-APR2 (SEQ ID NO: 25) and GCIRSL-APR3 (SEQ ID NO: 26), and b) detecting any amplified nucleic acid product, wherein detection of amplified product indicates the presence of *Neisseria gonorrhoeae*.

44. The method of claim 43 wherein said nucleic acid amplification reaction is a Strand Displacement Amplification (SDA) reaction.

45. The method of claim 44 wherein said SDA reaction utilizes GCIRSL-BL (SEQ ID NO: 27) and GCIRSL-BR (SEQ ID NO: 28) as bumpers.

46. The method of claim 43 wherein detecting said amplified nucleic acid product is conducted by hybridizing said amplified nucleic acid product with a detector selected from the group consisting of GCIRSL-DL1 (SEQ ID NO: 29), a complementary nucleic acid of SEQ ID NO: 29, GCIRSL-DL2 (SEQ ID NO: 30), a complementary nucleic acid of SEQ ID NO: 30, GCIRSL.FD1 (SEQ ID NO: 31) and a nucleic acid complementary to SEQ ID NO: 31.

47. The method of claim 44 wherein said SDA reaction is a thermal Strand Displacement Amplification (tSDA) reaction.

48. The method of claim 47 wherein said tSDA reaction is a homogeneous fluorescent real time thermal SDA reaction.

49. The method of claim 48 wherein said homogeneous real time tSDA reaction utilizes GCIRSL-BL (SEQ ID NO: 27) and GCIRSL-BR (SEQ ID NO: 28) as bumpers.

50. The method of claim 49 wherein said first primer is GCIRSL.APL1 (SEQ ID NO: 22) and said second primer is GCIRSL.APR3 (SEQ ID NO: 26).

51. The method of claim 50 wherein detecting said amplified nucleic acid product is conducted by hybridizing said amplified nucleic acid product with detector GCIRSL.FD1 (SEQ ID NO: 31).

52. A method for detecting the presence or absence of *Neisseria gonorrhoeae* in a sample wherein said method comprising the steps of a) treating said sample using a pair of nucleic acid primers in a nucleic acid amplification reaction wherein a first primer is selected from the group consisting of O2AL44.1 (SEQ ID NO: 32) and O2AL42.1 (SEQ ID NO: 33) and a second primer is selected from the group consisting of O2AR46.1 (SEQ ID NO: 34) and O2AR42.1 (SEQ ID NO: 35), and b) detecting any amplified nucleic acid product, wherein detection of amplified product indicates the presence of *Neisseria gonorrhoeae*.

53. The method of claim 52 wherein said nucleic acid amplification reaction is a Strand Displacement Amplification (SDA) reaction.

54. The method of claim 53 wherein said SDA reaction utilizes O2BL42.1 (SEQ ID NO: 36) and O2BR42.1 (SEQ ID NO: 37) as bumpers.

55. The method of claim 52 wherein detecting said amplified nucleic acid product is conducted by hybridizing said amplified nucleic acid product with a detector selected from the group consisting of O2DL42.1 (SEQ ID NO: 38), a complementary nucleic acid of SEQ ID NO: 38, O2DR42.1 (SEQ ID NO: 39) and a complementary nucleic acid of SEQ ID NO: 39.

56. The method of claim 53 wherein said SDA reaction is a tSDA reaction.

57. The method of claim 56 wherein said tSDA reaction utilizes O2BL42.1 (SEQ ID NO: 36) and O2BR42.1 (SEQ ID NO: 37) as bumpers.

58. The method of claim 57 wherein detecting said amplified nucleic acid product is conducted by hybridizing said amplified nucleic acid product with a detector selected from the group consisting of O2DL42.1 (SEQ ID NO: 38), a complementary nucleic acid of SEQ ID NO: 38, O2DR42.1 (SEQ ID NO: 39) and a complementary nucleic acid of SEQ ID NO: 39.

* * * * *